United States Patent
Falcão de Aragão et al.

(10) Patent No.: US 8,618,245 B2
(45) Date of Patent: Dec. 31, 2013

(54) PREPARATION OF PHA (POLYHYDROXYALKANOATES) FROM A CITRIC RESIDUE

(75) Inventors: Glaucia Maria Falcão de Aragão, Florianópolis SC (BR); Willibaldo Schimidell Netto, Florianópolis SC (BR); Jaciane Lutz Ienczak, Florianópolis SC (BR); Mônica Lady Fiorese, Curitiba PR (BR); Francieli Dalcaton, Florianópolis SC (BR); Franciny Schmidt, Florianópolis SC (BR); Ricardo Deucher, Brusque SC (BR); Cinthia Vecchi, Presidente Prudente SP (BR); Rafael Costa Rodrigues, Porto Alegre RS (BR)

(73) Assignees: Citrosuco S/A Agroindustria, Matao SP (BR); Universidade Federal de Santa Catarina, Florianopolis, SC (BR)

( * ) Notice: Subject to any disclaimer, the term of this patent is extended or adjusted under 35 U.S.C. 154(b) by 151 days.

(21) Appl. No.: 12/996,155

(22) PCT Filed: Nov. 18, 2008

(86) PCT No.: PCT/BR2008/000342
§ 371 (c)(1),
(2), (4) Date: May 10, 2011

(87) PCT Pub. No.: WO2009/149525
PCT Pub. Date: Dec. 17, 2009

(65) Prior Publication Data
US 2011/0301325 A1 Dec. 8, 2011

(30) Foreign Application Priority Data
Jun. 9, 2008 (BR) ...................................... 0801845

(51) Int. Cl.
*C08F 6/00* (2006.01)

(52) U.S. Cl.
USPC ............... 528/480; 435/135; 528/14; 528/15; 528/16; 528/55; 528/56; 528/179; 528/274; 528/495

(58) Field of Classification Search
USPC .......... 435/135; 528/274, 495, 14–16, 55–56, 528/179
See application file for complete search history.

(56) References Cited

U.S. PATENT DOCUMENTS

2007/0161096 A1* 7/2007 Mantelatto et al. ........... 435/135

OTHER PUBLICATIONS

International Preliminary Report on Patentability for Application No. PCT/BR2008/000342 dated Nov. 10, 2010.
International Search Report and Written Opinion for Application No. PCT/BR2008/000342 dated May 20, 2009.
Written Opinion for Application No. PCT/BR2008/000342 dated Sep. 8, 2010.
Lugg, H. et al., *Polyhydroxybutyrate Accumulation by a Serratia sp.*, Bioltechnology Letters, vol. 30, (2007), pp. 481-491.
MatiasMatias, F. et al., *Produção de PHB e PHDd a partir de Pectina e Ácido Cítrico e Reiiduos Agro-industriais contendo estes Substratos*, VI Sinaferm 2007—XVI Simpósio Nacional de. Bioprocesssos, (2007), 12 pages.
Spier, M. R. et al., *Phytase Production Using Citric Pulp and Other Residues of the Agroindustry in SSF by Fungal Isolates*, Food Technology and Biotechnology, vol. 46, (2008), pp. 178-182.
Tavares, L. Z. et al., *Production of Poly(3-hydroxybutyrate) in an Airlift Bioreactor by Ralstonia Eutropha*, Biochemical Engineering Journal, vol. 18, (2004), pp. 21-31.
Yu, P. H. F. et al., *Transformation of Industrial Food Wastes into Polyhydroxyalkanoates*, Water Science and Technology, vol. 40, (1999), pp. 365-370.
Zhang, Y. et al., *Biosynthesis of Poly-3-Hydroxybutyrate With a High Molecular Weight by Methanotroph From Methane and Methanol*, Journal of Natural Gas Chemistry, vol. 17, (2008), pp. 103-109.
MatiasMatias, F. et al., *Produção de PHB e PHDd a partir de Pectina e Ácido Cítrico e Reiiduos Agro-industriais contendo estes Substratos*, VI Sinaferm 2007—XVI Simpósio Nacional de Bioprocessos, (2007), 12 pages.

* cited by examiner

*Primary Examiner* — Gregory Listvoyb
(74) *Attorney, Agent, or Firm* — Alston & Bird LLP

(57) ABSTRACT

The present invention relates to an obtainment process of biodegradable polymers from a citric residue resulting from the processing of orange juice. The polymers obtained are polyesters classified as polyhydroxyalkanoates including, among them the poly(3-hydroxybutyrate) and poly(3-hydroxybutyrate-co-3-hydroxyvalerate). The biodegradable polymer is obtained from the batch culture process or fed batch culture process with or without recirculation of the cells, using as a carbon source the pre-treated pressing liquor and/or the citric molasses. The polyhydroxyalkanoates, herein described, can be used as substitutes of the synthetic polyesters in different areas, including the food, pharmaceutical, medical, agricultural and other areas.

18 Claims, 2 Drawing Sheets

PREPARATION OF PHA (POLYHYDROXYALKANOATES) FROM A CITRIC RESIDUE

FIELD OF THE INVENTION

The present invention relates to an obtainment process of biodegradable polyesters from a citric residue resulting from the processing of oranges for the obtainment of juice. The polyesters herein described are polyhydroxyalkanoates (PHA) and can be used as substitutes of the synthetic polyesters in many areas, including the food, pharmaceutical, medical, agricultural and other areas.

DESCRIPTION OF THE ART STATUS

Currently, the usage of the plastic material is increasingly frequent. This material substitutes conventional raw materials such as paper, paperboard, glasses, and metals, due to its low cost and big durability. In its manufacturing, synthetic polymers are used, such as polypropylene, polyethylene, vinyl polychloride, polystyrene, and others. These polymers are easily molded (including in fibers and translucent thin threads), have a high chemical resistance and they are relatively elastics, and can be used in the manufacturing of products packages of fast discard, as well as in the production of durable goods.

Despite its big applicability, the plastics became a serious environmental issue. The main reason is its extended degradation time, at about 200 years, staying in the environment and damaging the decomposition process of the organic matter, in addition to contribute to the silting process of rivers and alteration of the natural course of the riverbed. In mangrove areas, it jeopardizes the reproductive cycle of the animals and crustaceans.

The increase in the usage of synthetic polymers has resulted in the need to create alternatives in order to minimize the environmental issues generated by them. Among these alternatives, we can mention the incineration, recycling, suitable storage and, recently, the substitution of synthetic polymers by biodegradable materials. The plastics incineration is generally used as a way to recover energy due to its high calorific power, but the release of carbon dioxide and other components resulting from the burn jeopardize the environment, increasing the atmospheric pollution level. The recycling of the synthetic polymers is the most used alternative because it provides a reduction in the costs of up to 70%, when compared to the production of the petroleum-derived synthetic polymer. In relation to the biodegradable materials, one important option is the manufacture of polyhydroxyalkanoates (PHA). The polyhydroxyalkanoates have thermoplastic properties similar to those presented by the synthetic polymers, which can be applied in many types of products.

The polyhydroxyalkanoates (PHA) are a broad-usage polyesters which, because they are biodegradable, they have a lower polluter potential. The polyhydroxyalkanoates present very interesting characteristics, such as thermoplastic and physical-chemical properties very similar to those presented by the petrochemical-origin plastics, mainly in relation to the polypropylene. The polyhydroxyalkanoates present advantages to be fully biodegradable and biocompatible, to be produced from renewable raw materials, which can be recycled and incinerated without the generation of toxic products and, therefore, they are considered as a high applicability in relation to the petrochemical plastics.

The polyhydroxyalkanoates share different properties according to its monomeric composition. They are lipophilic substances accumulated inside PHA-producers microorganisms, found as insoluble inclusions and being extracted under the form of an odorless powder.

The general structure of the polyhydroxyalkanoates is given by the repetition of the following general formula,

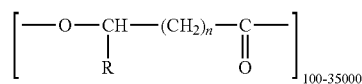

when the radical R can vary from one only hydrogen atom up to $C_{12}$, which can have instaurations, aromatic groups or also bounds to elements such as fluorine, chloride, and chrome.

The composition of the radical R, associated to the n value, determines the identity of the monomeric unit, the type, the number of repetitions of this unit and the properties of the biodegradable polymer.

In accordance with the carbonic chains length and its monomeric units, the polyhydroxyalkanoates are classified in three groups:

1. Polyhydroxyalkanoates constituted by units of hydroxyalkanoic acids of short chain ($PHA_{SSC}$), i.e., those which have a carbon chain constituted of 3 to 5 C atoms;
2. Polyhydroxyalkanoates constituted by units of hydroxyalkanoic acids of mean chain ($PHA_{MCL}$), i.e., those which have a carbon chain constituted of 6 to 14 C atoms;
3. Polyhydroxyalkanoates constituted by units of hydroxyalkanoic acids of long chain ($PHA_{LCL}$), i.e., those which have carbon chain constituted of more than 15 C atoms.

The polyhydroxyalkanoates (PHA) most known are, mainly, the poly(3-hydroxybutyrate) (P(3HB)) and the poly(3-hydroxybutyrate-co-3-hydroxyvalerate) (P(3HB-co-3HV)).

The polyhydroxyalkanoates are considered as a great industrial interest as biodegradable plastics and/or biocompatible for different application areas. The desirable properties to the different applications of a plastic material are high melting point, low hardness, high resistance to pressure, resistance to the elongation before the disruption and high resistance to impact.

Due to the characteristics they have, P(3HB) and P(3HB-co-3HV) were initially used in the manufacturing of bottles, films and fibers for biodegradable packages, as well as plants protection bags. These biopolymers also have an application in the medical area, such as osteosynthetic materials and surgical sutures, reposition of blood vessels and bandages. Other applications include the fact to be used as a biodegradable vehicle for the application of drugs, medications, insecticides, herbicides or fertilizers and fragrances or yet as packages, films, bags and containers.

The polyhydroxyalkanoates can be produced by different unicellular microorganisms in the form of intracellular granules as a reservation of carbon and energy. The microorganisms capable to produce and accumulate PHA are mainly bacteria that can be found in the nature, i.e., in the soil, sea water, effluents, etc. Such microorganisms are those pertaining to different taxonomic groups of different genres, such as methylotrophic microorganisms, *Azobacter, Alcaligenes, Pseudomonas, Burkholderia*, in addition to *Escherichia coli* recombinant.

The most used microorganisms are: *Alcaligenes latus, Pseudomonas oleovorans, Azobacter vinelandii, Cupriavidus necator, Burkholderia sacchari*, a number of strains of *methylotrophus* and *Escherichia coli* recombinant. The PHA can also be produced by transgenic plants.

For the extraction process of the polymer not to be costly, it is necessary for the strain to be capable to accumulate at least 60% of its cellular mass in polymer. This way, all Gram-positive bacteria are eliminated and those with low capacity of synthesis and accumulation of polymer for the industrial production.

Since the discovery of polyhydroxyalkanoates producer bacteria by Lemoigne in 1926, the Gram-negative bacteria *Cupriavidus necator* is the most well studied representative in this group, and the biggest PHA producer until today. Before being classified with this name, *Cupriavidus necator* was previously described as *Hydrogenomonas eutropha*, *Alcaligenes eutrophus*, *Ralstonia eutropha* and *Wautersia eutropha*. Its broad usage is due to the high ability to accumulate big quantities of PHA from simple sources of carbon, such as acetic acid, fructose and glucose.

The production of PHA occurs when the microorganism grows in disbalanced conditions of culture. These conditions can be associated to the nutrients limitation (such as N, P, $O_2$, K and Mg) in the presence of an excessive carbon source or physical limitations, such as temperature and concentration of diluted oxygen.

In a balanced growth condition, *C. necator* uses substrates such as carbohydrates, pyruvate or acetate, starting the regulation mechanism by the acetyl-CoA enzyme. As a first step, the β-cetotiolase enzyme leads to the condensation of two molecules of acetyl-CoA in acetoacethyl-CoA. In the second step, a NADPH-dependent acetoacethyl-CoA reductase leads to a conversion of R-3-hydroxybutyryl-CoA, by a stereoselective reaction. The third and last step is the catalyzed polymerization by the PHA synthase. The biosynthesis of the copolymer by *C. necator* only occurs when there are precursor substrates of the unit 3HV, which can be converted in propionyl-CoA or 3-hydroxyvalery-CoA, as a propionic acid, valeric acid or pentanoic acid.

From these metabolic characteristics, the production of polyhydroxyalkanoates occurs in two phases: a first phase of cellular growth in a balanced culture medium aiming at the increasing of the biomass and a second phase, where the limitation of an essential nutrient—not a source of carbon—occurs, in general nitrogen, phosphor and oxygen addressing the metabolism for the production of PHA. In order to proportionate the production of copolymer, the addition of one of the precursors agents previously mentioned must be performed during the second process phase.

P(3HB) production strategies to increase the content of biopolymer and to decrease the total cost of bioplastics are necessary. The usage of low-cost substrates can represent 40% of economy in the production process of P(3HB). One interesting alternative is the usage of agroindustrial residues. Among the low-cost substrates, the residues deriving from plants of food processing such as the starch, sugar cane and whey are those of a higher highlight.

Regarding the industrial production of PHA, several documents are found comprising its obtainment through the usage of renewable carbon sources in the form of agroindustrial residues. The residues described include apple bagasse, whey, whey mixture and inverted sugar, residue of the potatoes processing industry (hydrolyzed starch) and others. The usage of these low-cost residues contributes for the reduction of the final price of these biopolymers.

The document PI0501139-6 describes the production process of PHA from vegetal oils, glycerol, residual mono-, di- or triglycerides, arising from the production of biodiesel obtained from vegetal oils.

The document PI0504054-0 describes the production process of short-chain PHA and especially the poly(3-hydroxybutyrate) from vegetal oil such as, for example, soybean oil. In the process described, the concentration of vegetal oils can not be superior to $0.3 \text{ g·L}^{-1}$ of oleic acid due to the fact that it causes inhibition of the microorganism growth. This limitation makes this process very restricted.

The document US 2006/0088921 refers to a production method of PHA from the organic garbage. The method includes a pre-treatment of the organic residues with acidogenic microorganisms, followed by the culture process for the production of PHA by specific microorganisms, including *R. eutropha*, *P. oleovorans* and others. Although theoretically viable, the production of PHA from this organic matter is hindered by the diversity and complexity of the substrate used, making the process not viable.

The document PI0207356-0 describes the production process of polyhydroxybutyrate and its copolymer polyhydroxybutyrate-co-hydroxyvalerate from the sugar cane bagasse. Although it is a raw material that presents a big offer, the sugar cane bagasse must be initially hydrolyzed for the obtainment of a culture medium suitable for the production of PHA.

The pre-treatment of lignocellulosic biomass consists of one of the most relevant operational stages in terms of direct cost, in addition to influence the previous and subsequent stages of the process. The pre-treatment can generate inhibitor products to the microorganism and a vast quantity of suspended solids, making the process inefficient and/or presenting low productivity.

The document entitled "Production of poly(3-hydroxybutyrate) from inexpensive substrates" (Enzyme and Microbial Technology Vol. 27, (10), 2000, Pages 774-777) describes the production of a PHA, the Poly(3-hydroxybutyrate) P(3HB) from the starch and protein whey, both residues resulting from industrial processes of food. The starch is previously hydrolyzed in a two-step process, including liquefaction and saccharification. The substrate prepared is submitted to a biotechnological process using *A. chroococcum* and *E. coli* recombinant. The article further highlights the relevance of the usage of the raw materials as a form to decrease the production cost of the P(3HB).

Although it is theoretically possible to produce PHA from several types of agroindustrial residues, some factors such as the availability of fermentescible sugar, the presence of inhibitors and the treatment of lignocellulosic material, can make the process not viable.

The usage of residues, as those herein described, demands, oftentimes, as a pre-requirement, the previous treatment of the raw material used, including the hydrolysis of the long-chain sugars in order to make possible the assimilation of the carbon source by the microorganisms producing polyhydroxyalkanoates. This process of hydrolysis normally involves a long time of preparation, the usage of enzymes or acid and, oftentimes generates inhibitors components of cultivation, causing additional costs to the production process of the relevant PHA.

The invention herein described contour the problems previously mentioned through the usage of an obtainment process of PHA from residues of the orange juice processing, comprising a simplified pre-treatment of the raw material and without hydrolysis. The invention makes viable the usage of an agroindustrial residue until that time less used, increasing its added value and, consequently, making the process profitable, in addition to ecological.

BRIEF DESCRIPTION OF THE INVENTION

The present invention refers to an obtainment process of polyhydroxyalkanoates (PHA) from the citric residue resulting from the processing of oranges for the obtainment of juice. The relevant process comprises the following steps:

a) obtainment of pressing liquor and/or citric molasses;
b) physical-chemical treatment of the material obtained in the step a;
c) preparation of a culture medium for the production of PHA;
d) culture process conduction.

The invention also refers to the usage of citric residue for the production of PHA, in accordance with the process described in the invention. The invention yet refers to PHA or to a polymeric composition containing PHA obtained from the process described in the invention.

The present invention also refers to a solid artifact comprising PHA obtained from the process for the production of PHA described in the invention, as well as a solid artifact containing a polymeric mixture that comprises PHA obtained according to the process for the production of PHA described in the invention.

DETAILED DESCRIPTION OF THE INVENTION

The present invention presents a simple process of PHA production, from an abundant agroindustrial residue and easy to manipulate. The relevant process uses the residue of the oranges processing, denominated citric residue, contributing considerably for the reduction of the environmental impact of this residue, as well as increasing the added value of it. The orange juice extraction generates, as a residue, around 52% of fresh citric pulp, with 73% to 83% of humidity. The citric pulp is constituted by peel (60%-65%), said pulp, the bagasse (30%-35%), and the seeds (about 10%). With the increase of the productive scale of orange juice and the generation of big volumes of residues, the first problems of environmental contamination started, which has stimulated the development of usage strategies of the residue generated. An alternative developed for the partial usage of the generated liquid residue, constituted by proteins, essential oils, pectins, sugars, organic acids and salts; was the alcoholic fermentation for the production of ethanol. Although the production of ethanol has minimized the environmental impact caused by the generation of residues from the extraction process, the aggregation of a higher value to it would represent a considerable gain in the competitiveness within the productive context.

The present invention presents a process of obtainment of PHA from citric residue, comprising the following steps:

a) obtainment of pressing liquor and/or citric molasses;
b) physical-chemical treatment of the material obtained in step a;
c) preparation of the culture medium for the production of PHA;
d) conduction of the culture process.

The citric residue described in the invention corresponds to the skin, the pulp, and seeds resulting after the pressing of oranges to extract juice.

The pressing liquor and/or citric molasses of the present invention are obtained from the citric residue. The citric residue, after obtained, is submitted to a milling process, treatment with calcium oxide (CaO) and pressing obtaining, as a result, the pressing liquor. Other agents, in addition to CaO, that have the property of hydrolyzing the pectin for the water release and to facilitate the pressing process can also be used.

Figure 1:
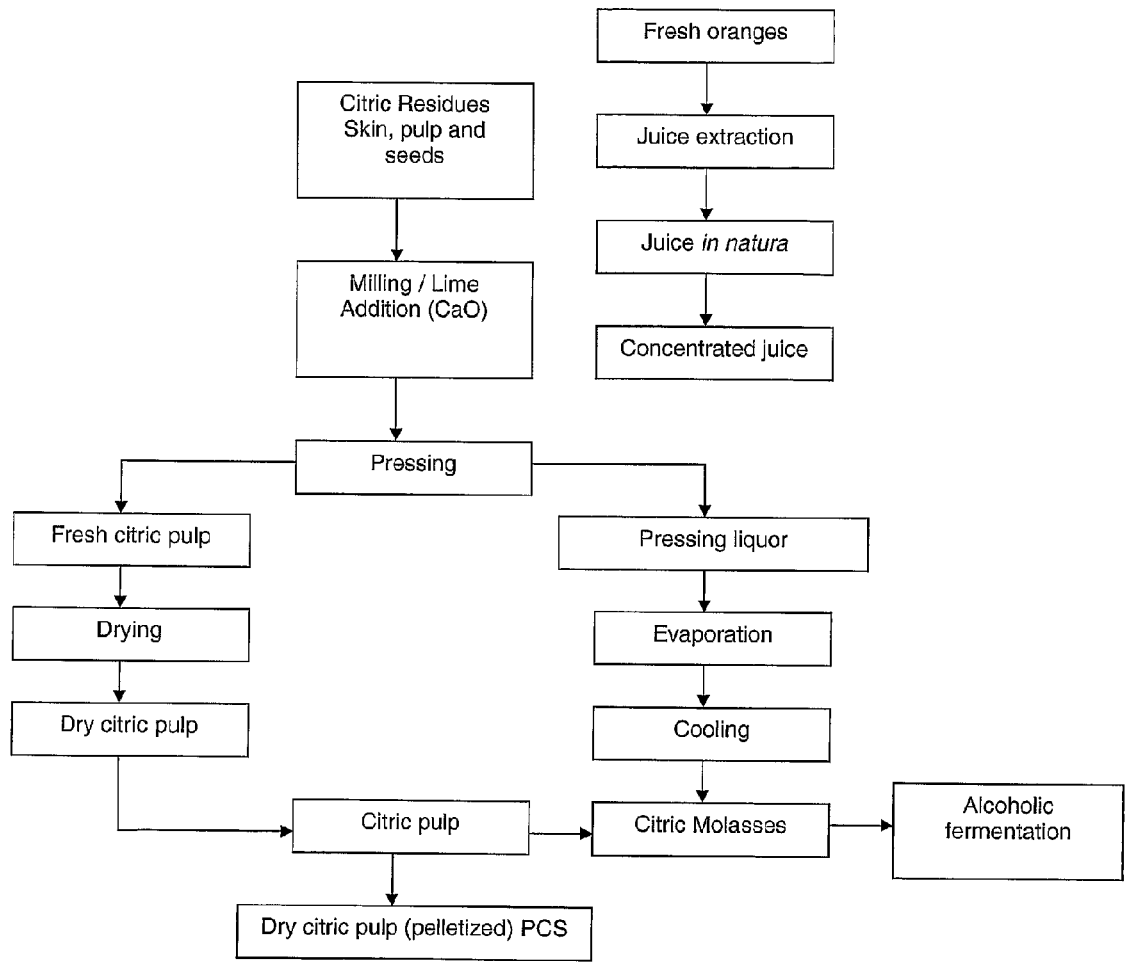
FIG. 1 is a flow chart showing a process for obtaining polyhydroxcyalkanoates (PHA) in accordance with an embodiment of the present invention.

The pressing liquor obtained can also go through a concentration process, followed by a cooling process, thus obtaining the citric molasses. Preferably, the concentration of the pressing liquor takes place through the evaporation. The obtainment steps of citric residue, pressing liquor and citric molasses as previously described, can be viewed in FIG. 1.

The pressing liquor and/or citric molasses obtained in the step a of the obtainment process of PHA are used as a culture medium of microorganisms in the production process of PHA of the present invention. For the usage of the pressing liquor and/or citric molasses as a culture medium it is necessary, initially, that these raw materials are submitted to a previous physical-chemical treatment. The physical-chemical treatment by which the pressing liquor and/or citric molasses is submitted comprises the centrifugation of it, followed by a step of sterilization or pasteurization of the material. After the sterilization or pasteurization, the material free of microorganisms goes through a decantation process followed by a removal of the supernatant material. The supernatant material is then used for the preparation of the culture medium. Optionally, pressing liquor and/or citric molasses can suffer a pH correction previous to the centrifugation. Preferably, the pH 7.0 is chosen for correction. In a preferred substantiation of the invention, the centrifugation of the pressing liquor and/or citric molasses takes place at the temperature of 5° C. and the sterilization takes place at 121° C. for 15 minutes. In another preferred substantiation of the invention, the centrifugation of the pressing liquor and/or citric molasses takes place at the temperature of 5° C. and the pasteurization takes place at 113° C. for 2 minutes. In another preferred substantiation of the invention, the centrifugation takes place aseptically and is followed by an aseptically filtration. The material aseptically filtrated is submitted to a decantation process followed by the removal of the supernatant material. The supernatant material is then used for the preparation of the culture medium. In another preferred substantiation of the invention, the initial pH of the pressing liquor and/or citric molasses is corrected for 7.0 and the resulting material is centrifuged to 3500 rpm for 5 min. After the centrifugation, the supernatant is heated at 100° C. and then submitted to a cold decantation with the removal of the supernatant. The supernatant material is then used for the preparation of the culture medium. In one more preferred substantiation of the invention, the pressing liquor and/or citric molasses is submitted to the centrifugation at 5° C. and pasteurization at 113° C. for 2 min. After pasteurization, the pressing liquor and/or citric molasses are then submitted to the cold decantation and the supernatant is submitted again to the pasteurization process at 113° C. for 2 minutes. The resulting material is then used for the preparation of the culture medium. In other preferred substantiation of the invention, the physical-chemical treatment of the pressing liquor and/or citric molasses consists in the filtration of it in a membrane of the micro filtration, or ultra filtration, or submitted to the separation of the suspended solids by flotation.

The pressing liquor and/or citric molasses submitted to physical-chemical treatment are used for the preparation of the culture medium of the production process of PHA of the present invention. The preparation of the culture medium takes place, initially, through the addition, to the supernatant material resulting from the physical-chemical treatment of the pressing liquor and/or citric molasses, of nutrients essential to the culture process selected among nitrogen, phosphor, sulphur, magnesium, potassium, oxygen, oligonutrients or mixture of them. Preferably, the additional oligonutrients during the preparation of the culture medium of the invention, are selected among molybdenum, manganese, cobalt, zinc, nickel, copper and boron.

Alternatively, after the addition of the nutrients, the culture medium can be submitted to a sterilization process in order to guarantee the asepsis/conduction of the culture process. In a preferred substantiation of the invention, the sterilization process of the culture medium with nutrients takes place at 121° C. for 15 minutes.

Figure 2:
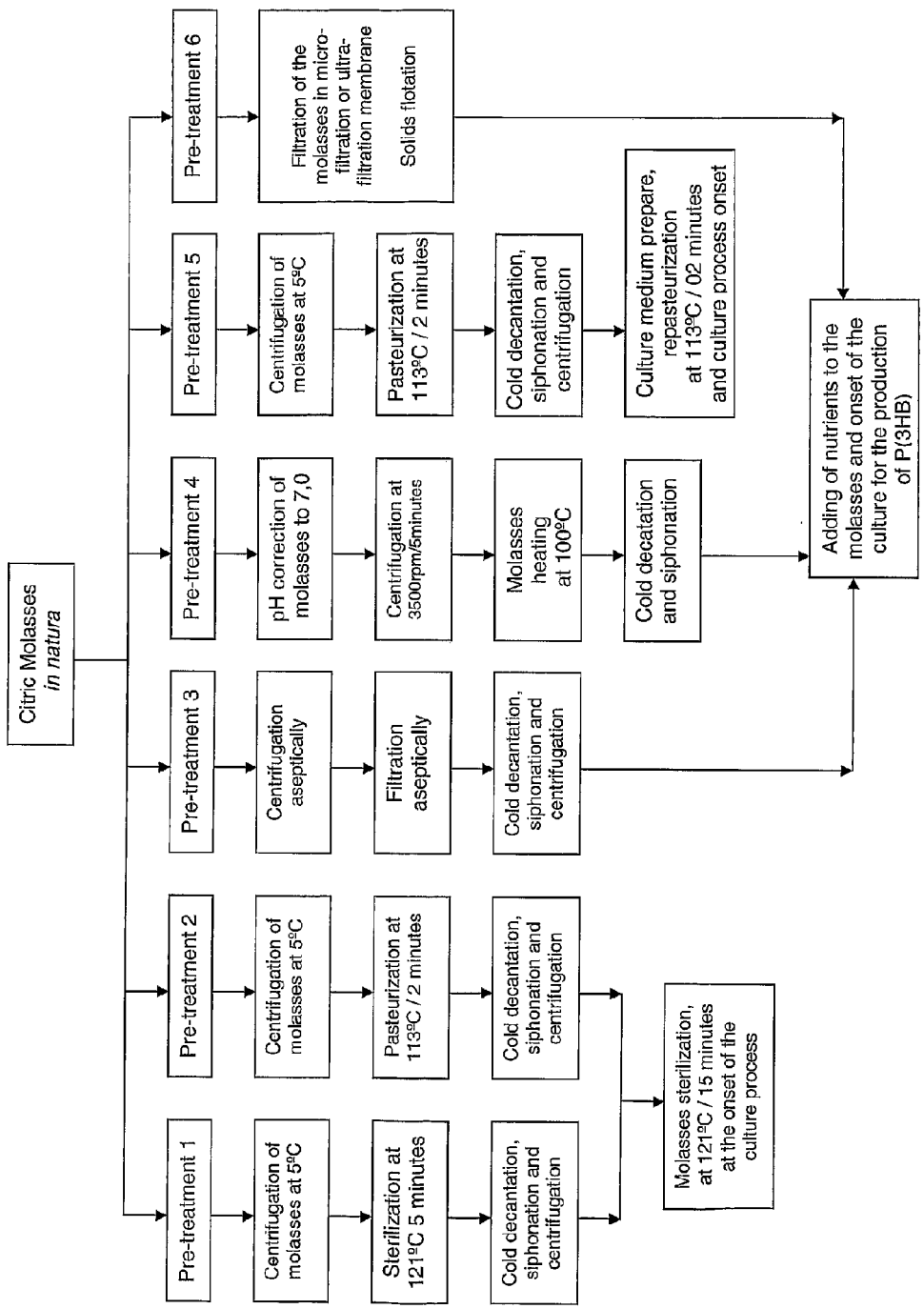
FIG. 2 is a chart showing a process for obtaining polyhydroxcyalkanoates (PHA) in accordance with an embodiment of the present invention.

The stages of physical-chemical treatment of the pressing liquor and/or citric molasses, as well as the preferred substantiations previously described, can be viewed in FIG. 2.

The culture medium, used in the biotechnological process described in the present invention, must comprise an initial tenor of sugars reductors of 10 to 60 g·L$^{-1}$. For the conduction of the biotechnological process, microorganisms pertaining to different taxonomic groups: *Azotobacter*, methylotrophic microorganisms, *Alcaligenes, Pseudomonas, Burkholderia*, in addition to *Escherichia coli* recombinant can be used. Preferably, the microorganisms used in the present invention are selected among *Alcaligenes latus, Pseudomonas oleovorans, Azobacter vinelandii, Bacillus cereus, Cupriavidus necator, Burkholderia sacchari, methylotrophus* and *Escherichia coli* recombinant. Even more preferably, the biotechnological process of the present invention is conducted through the usage of *Cupriavidus necator*. For the biotechnological process to be successful, both in the microorganisms' production and in the polymer production, two pre-inocula are necessary, preceding the reactor process. The first pre-inoculum, must preferably be executed through the propagation of the microorganism *Cupriavidus necator* in a culture medium containing nutrient broth comprising 5 g·L$^{-1}$ of peptone, 3 g·L$^{-1}$ of meat extract. This pre-inoculum is kept in a rotator shaker to the temperature, rotation and time compatible to the process. Preferably, the first pre-inoculum is maintained at 30° C. under agitation of 150 rpm for 24 h. After this period, 10% of the final volume to be used in the culture process is transferred from the first pre-inoculum to the second pre-inoculum. The second pre-inoculum is characterized by containing mineral salts and essential nutrients to the microorganism growth. This pre-inoculum is kept in specific conditions of temperature, agitation and time, compatible to the process. Preferably, the second pre-inoculum is kept at 30° C., 150 rpm for 24 h. After this period, a pre-inoculum volume, sufficient for the conduction of the culture process, is added to the reactor containing the culture medium prepared according to what is previously described. Preferably, the volume of the second pre-inoculum which is added to the reactor, corresponds to mainly 10% of the volume of the culture medium to be used in the culture process.

The biotechnological process for the production of PHA of the present invention can be conducted through the batch culture process or in fed batch culture process. The process can be executed with or without recirculation of the cells for the reactor, in order to obtain a high cellular density. The process of the present invention comprises the stages of cellular growth followed by the stage of induction to the production of PHA. The culture process is conducted at the temperature of 25° C. to 40° C. During the culture process, the pH can vary between 7.2 and 5.4 and the culture medium is agitated at a velocity of 200 to 1000 rpm. During the conduction of the culture process, the content of diluted oxygen can vary between 10% and 100% of saturation of the culture medium with atmospheric air, this condition not being inferior to 10%.

The induction stage to the production takes place through the imposition of the limitation of a nutrient (nitrogen, phosphor, sulphur, magnesium, potassium or oxygen). This limitation takes place during the conduction of a culture process and must take place preferably after the obtainment of a minimum biomass concentration between 15 g·L$^{-1}$ to 60 g·L$^{-1}$ (dry weight). The determination of the initial concentration of the nutrient limiting in the culture medium must consider the conversion factors of the nutrients in cells. The polymer recovery (PHA) can be executed by different methods compatible to the culture process of the invention. These methods include the separation of the cellular material containing the polymer followed by an extractive process.

The present invention also refers to the usage of citric residue for the production of PHA using the obtainment process of PHA described previously. Further an object of the present invention is the PHA itself, obtained from the process described in the invention. The invention also refers to a polymeric composition comprising PHA obtained from the process described in the invention.

The present invention yet refers to a solid artifact, comprising PHA obtained from the process for the production of PHA described in the invention, as well as a solid artifact containing a polymeric mixture that comprises PHA obtained in accordance with the process for the production of PHA described in the invention.

Some possibilities of substantiation of the relevant invention are described as follows. The examples herein described must be interpreted as possibilities of substantiation of the invention and must not be used, however, to limit the scope of protection of it.

Example I

The first pre-inoculum was cultured in a Nutrient Broth kept in a rotator shaker for 24 hours. After this time, a volume equivalent to 10% of the final volume to be used in the culture process was transferred from the first to the second pre-inoculum, which is constituted of a mineral salts medium and nutrients adequate for the cellular growth of the microorganism used. This second pre-inoculum was kept in a rotator shaker, at 30° C. and 150 rpm for 54 hours. After this time, a volume equivalent to 10% of the final volume to be used in the culture process was transferred from the second pre-inoculum for the 5-liter reactor containing the medium composed by pressing liquor and/or citric molasses. The pressing liquor and/or citric molasses contains around 60 to 80 g·L$^{-1}$ of ART (total reductor sugars), due to this reason, it must be diluted in a distilled water for the obtainment of a concentration of reductor sugars between 10-60 g.$^{L-1}$ (growth limit for the *C. necator*), added with mineral salts and nutrients for the growth. The pre-treatment 5 (FIG. 2) was employed for the reduction of suspended solids present in the pressing liquor and/or citric molasses. The culture process was performed with the initial concentration of total reductor sugars (ART) between 10 and 40 g·L$^{-1}$, the temperature between 25 and 40° C., pH ranging from 5.4-7.0, agitation from 200 to 900 rpm, oxygen concentration between 10 to 100% of the saturation with atmospheric air, for 28 hours of culture. The conversion factor of the substrate in cell ($Y_{x/s}$) obtained was about 0.54 g·g$^{-1}$, the growth specific speed obtained was 0.44 h$^{-1}$. The production of P(3HB) had an increase from the tenth (10$^{th}$) hour when the exhaustion of nitrogen occurred. The total biomass was 17.1 g·L$^{-1}$. The percentage of P(3HB) in the cell at the end of the culture process was 81%, with a mean productivity of P(3HB) of 0.49 g·L$^{-1}$·h$^{-1}$, in 18 hours of production. The recovery of polymer was executed with the separation of the cells from the liquid to the conclusion of the culture process through centrifugation. The extraction was executed with a relation to the cells mass and solvent volume, for example, chloroform ("Optimization of microbial poly(3-hydroxybutyrate) recovery using dispersions of sodium hypochlorite solution and chloroform"—Biotechnology and Bioengineering, v. 44, pp. 256-261, 1994) ranging from 1:2 in the temperatures of 20° C. up to 60° C. with a magnetic agitation, agitation in shaker or without agitation. The percentage of recovery had ranged from 80 to 98%.

Example II

The usage of pressing liquor of the orange bagasse was tested for the production of P(3HB) as a sub-product of the orange juice industry, without the application of a thermal treatment. The first pre-inoculum was cultured in a nutrient broth, kept in a rotator shaker at 30° C. and 150 rpm for 24 hours. After its activation, an equivalent volume at 10% of the final volume to be used in the culture process was transferred from the first to the second pre-inoculum, which is constituted of mineral salt medium and nutrients adequate for the cellular growth of the microorganism used. This second pre-inoculum was kept in a rotator shaker, at 30° C. and 150 rpm for 24 hours. After this time, a volume equivalent to 10% of the final volume to be used in the culture process was transferred from the second pre-inoculum to the 5-liter reactor containing pressing liquor presenting about 10 and 60 g·L$^{-1}$ of reductor sugars. This medium was further added mineral salts and nutrients for the growth.

The culture process was executed for 32 hours, the culture process temperature was kept at 30° C., the pH was kept between 5.4 and 7.0, the agitation ranged from 400-900 rpm, the oxygen concentration remained between 10 and 100% of the saturation value with atmospheric air during the culture process. The growth specific velocity was about 0.24 h$^{-1}$, when the pressing liquor culture medium was used. The nitrogen exhaustion in the culture process took place at the 12$^{th}$ hour. The production phase was about 20 hours, with a final concentration of P(3HB) I the cell equal to 6.9 g·L$^{-1}$, with a mean productivity of 0.21 g·L$^{-1}$·h$^{-1}$ and productivity in the production phase of 0.27 g·L$^{-1}$·h$^{-1}$. The polymer percentage in the cell was 53%. The recovery of the polymer was executed with the separation of the cells from the liquid to the conclusion of the culture process through centrifugation. The extraction was executed with a relation of cells mass and solvent volume, for example, chloroform ("Optimization of microbial poly(3-hydroxybutyrate) recovery using dispersions of sodium hypochlorite solution and chloroform"—Biotechnology and Bioengineering, v. 44, pp. 256-261, 1994) ranging from 1:2 up to 1:20. The extraction time ranged from 1 to 4 hours at the temperatures of 20° C. up to 60° C. with a magnetic agitation, agitation in shaker or without agitation. The recovery percentage ranged from 80 to 98%.

Example III

The Nutrient Broth was used as a first pre-inoculum performed in a rotator shaker at 30° C. and 150 rpm for 24 hours. The volume equivalent to 10% of the final volume to be used in the culture process was transferred from the first to the second pre-inoculum which is constituted of mineral salts medium and nutrients adequate for the cellular growth of the microorganism used. This second pre-inoculum was kept in a rotator shaker, at 30° C. and 150 rpm for 24 hours. After this time, the cells were transferred to the 5-liter reactor containing the pressing liquor and/or citric molasses (about 60 to 80 g·L$^{-1}$ of ART) diluted in distilled water for the obtainment of a concentration of reductor sugars between 10-60 g·L$^{-1}$ and added with mineral salts and nutrients for the growth. The temperature of 35° C. was applied. The pH was kept in 7.0 and the agitation ranged from 400-900 rpm, the oxygen concentration remained superior to 20% of the saturation with atmospheric air for 26 hours of culture process. It was noted a production phase of 18 hours, with 9.76 g·L$^{-1}$ of P(3HB) and 18.16 g·L$^{-1}$ of total biomass. The conversion factor of the substrate in cells ($Y_{x/s}$) was 0.76 g·g$^{-1}$ and cell in product ($Y_{p/s}$) was 0.41 g·g$^{-1}$ resulting in a mean productivity of 0.46 g·L$^{-1}$·h$^{-1}$. The experiment had its final observed by the concentration value of ART below 5 g·L$^{-1}$. The production of P(3HB) had its increase from the eighth (8$^{th}$) hour when the nitrogen exhaustion took place. The percentage of P(3HB) in the cell at the end of the culture process was 54%. The polymer recovery occurred with the separation of the cells from the liquid at the end of the culture process through centrifugation. The extraction was performed with a relation of the cells mass and solvent volume, for example, chloroform ("Optimization of microbial poly(3-hydroxybutyrate) recovery using dispersions of sodium hypochlorite solution and chloroform"—Biotechnology and Bioengineering, v. 44, pp. 256-261, 1994) ranging from 1:2 up to 1:20. The extraction time ranged from 1 to 4 hours at the temperatures of 20° C. up to 60° C. with a magnetic agitation, agitation in shaker or without agitation. The recovery percentage ranged from 80 to 98%.

The invention claimed is:

1. Obtainment process of polyhydroxcyalkanoate (PHA) from the citric residue, wherein it comprises the following steps:
    a) obtaining a pressing liquor and/or citric molasses;
    b) physical-chemical treating of the material obtained in the step a to obtain a supernatant material;
    c) preparing a culture medium for the production of PHA wherein in the step c, the culture medium is prepared through an addition of essential nutrients to the culture process to the supernatant material and the added nutrients are selected among nitrogen, phosphor, sulphur, magnesium, potassium, oxygen, oligonutrients or a mixture of them;
    d) conducting a culture process on said culture medium at a temperature of 25° C. to 40° C., and wherein the oligonutrients are selected among molybdenum, manganese, cobalt, zinc, nickel, copper and boron, and a mixture of them.

2. Obtainment process of PHA in accordance to claim 1, wherein the citric residue corresponds to the skin, pulp and seed resulting from the oranges pressing to the juice extraction.

3. Obtainment process of PHA in accordance to claim 1, wherein in the step a, the pressing liquor is obtained from the milling/treatment with calcium oxide or agents that have the property to hydrolyze the pectin and pressing of the citric residue.

4. Obtainment process of PHA in accordance to claim 1, wherein in the step a, the citric molasses is obtained from the concentration of the pressing liquor followed by cooling.

5. Obtainment process of PHA in accordance to claim 4, wherein the concentration of the pressing liquor is performed through evaporation.

6. Obtainment process of PHA in accordance to claim 1, wherein in the step b the physical-chemical treatment of the pressing liquor and/or citric molasses occurs through the following sub-steps:

b1) centrifugation of the pressing liquor and/or citric molasses;
b2) sterilization or pasteurization of the material;
b3) decantation of the sterilized or pasteurized material, followed by the removal of the supernatant material.

7. Obtainment process of PHA in accordance to claim 6, wherein a correction step of pH of the pressing liquor and/or citric molasses is performed before the step b1.

8. Obtainment process of PHA in accordance to claim 1, wherein a sterilization or pasteurization step of the material takes place after the addition of nutrients to the culture medium.

9. Obtainment process of PHA in accordance to claim 1, wherein in the step c, the culture medium comprises an initial content of reductor sugars of 10 to 60 $g \cdot L^{-1}$.

10. Obtainment process of PHA in accordance to claim 1, wherein in the step d, the culture process is conducted through a batch culture process or fed batch culture process.

11. Obtainment process of PHA in accordance to claim 10, wherein the batch culture process or fed batch culture process is performed with a recirculation of the cells.

12. The Obtainment process of PHA from a citric acid residue comprising the steps of:
    a) obtaining a pressing liquor and/or citric molasses;
    b) physical-chemical treating of the material obtained in the step a;
    c) preparing a culture medium for the production of PHA;
    d) conducting a culture process on said culture medium;

wherein in the step d, the culture process takes place in the following steps:
    d1) step of cellular growth;
    d2) step of production induction of PHA, and wherein in the step d2, the induction to the production of PHA is initiated through the non-carbon sources nutrients limitation.

13. Obtainment process of PHA in accordance to claim 1, wherein in the step d, the pH can vary between 7.2 and 5.4.

14. Obtainment process of PHA in accordance to claim 1, wherein in the step d, the medium is agitated at a velocity from 200 to 1000 rpm.

15. Obtainment process of PHA in accordance to claim 1, wherein in the step d, the diluted oxygen concentration must be between 10% and 100% of the culture medium saturation with atmospheric air.

16. Obtainment process of PHA in accordance to claim 12, wherein at the beginning of the induction step, the concentration of the minimum biomass corresponds from 15 $g \cdot L^{-1}$ to 60 $g \cdot L^{-1}$.

17. Obtainment process of PHA in accordance to claim 12, wherein the non-carbon sources nutrients are selected among nitrogen, phosphor, sulphur, magnesium, potassium or oxygen.

18. Usage of citric residue for the production of PHA, wherein it occurs through the process as defined in claim 1.

* * * * *